United States Patent [19]

Telang

[11] Patent Number: 4,650,476
[45] Date of Patent: Mar. 17, 1987

[54] CHEST DRAINAGE APPARATUS WITH ADJUSTABLE SUCTION CONTROL

[75] Inventor: Anil M. Telang, Edison, N.J.

[73] Assignee: Becton, Dickinson and Company, Franklin Lakes, N.J.

[21] Appl. No.: 789,289

[22] Filed: Oct. 18, 1985

[51] Int. Cl.[4] ............................................. A61M 1/00
[52] U.S. Cl. ................................... 604/319; 604/321; 137/205
[58] Field of Search ............................... 604/318–321, 604/126; 137/205; 433/95

[56] References Cited

U.S. PATENT DOCUMENTS

| | | | |
|---|---|---|---|
| 3,750,692 | 8/1973 | Tibbs | 604/321 |
| 4,372,336 | 2/1983 | Cornell et al. | 137/205 |
| 4,439,190 | 3/1984 | Protzmann et al. | 604/319 |
| 4,468,226 | 8/1984 | Kurtz et al. | 604/321 |

FOREIGN PATENT DOCUMENTS 0111087  6/1984  European Pat. Off. ............ 604/319

OTHER PUBLICATIONS

Gore-Tex Membrane Products–"Expanded PTFE Membranes and Laminates", W. L. Gore & Assoc., Elkton, Maryland 21921, 1980, p. 6.

Primary Examiner—C. Fred Rosenbaum
Assistant Examiner—J. L. Kruter
Attorney, Agent, or Firm—John L. Voellmicke

[57] ABSTRACT

A chest drainage apparatus for draining fluid from a patient includes a collection chamber for collecting the fluid. An inlet port is in fluid communication with the collection chamber for receiving the fluid. A one-way valve is in fluid communication with the collection chamber for preventing air from entering the patient from the inlet port. A vacuum control chamber has a lower end and an upper end in fluid communication with the one-way valve. A flexible conduit has a first end fluid communication with the exterior of the apparatus and a second end movably positioned within the vacuum control chamber. Elevation adjustment apparatus connected to the flexible conduit is provided for moving the second end of the flexible conduit upwardly and downwardly to various positions within the vacuum control chamber and is activatable from the exterior of the chest drainage apparatus. A suction outlet port for communicating with a source of vacuum is in fluid communication with the vacuum control chamber.

22 Claims, 11 Drawing Figures

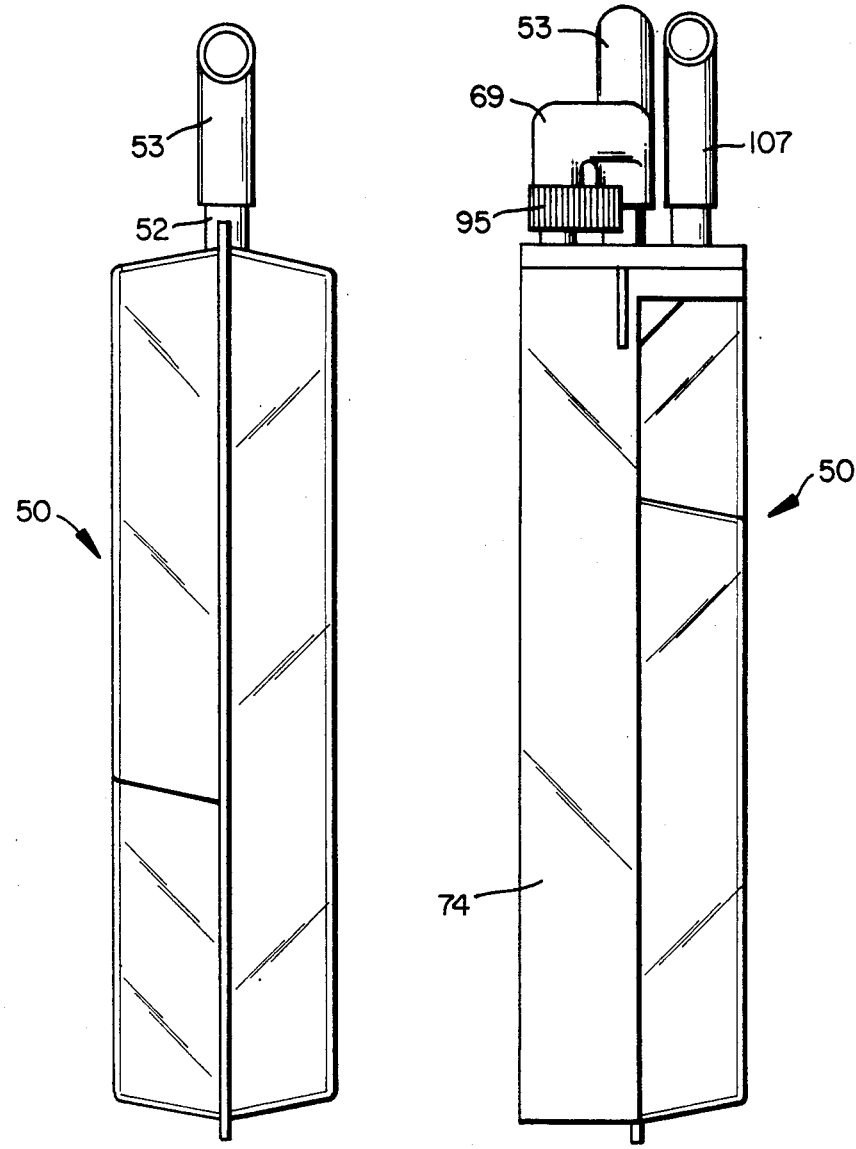

CHEST DRAINAGE APPARATUS WITH ADJUSTABLE SUCTION CONTROL

BACKGROUND OF THE INVENTION

1. Field of the Invention

The present invention relates to surgical drainage apparatus and more particularly relates to a chest drainage apparatus for draining fluid from the pleural cavity of a surgical patient.

2. Description of the Prior Art

Early prior art chest drainage systems consist of a series of serially connected glass bottles. One of these bottles is a graduated collecting bottle in fluid communication with the pleural cavity and in fluid communication with an underwater seal bottle via tubes passing through its cap or stopper. The underwater seal bottle contains a quantity of liquid, such as water, and a rigid tube which has one end positioned below the water surface and the other end in fluid communication with the collection bottle acting as an underwater seal. The underwater seal does not interfere with the drainage of liquid from the pleural cavity, but it functions as a one-way valve to prevent air from reentering the submerged tube and thereby reentering the patient's pleural cavity. In operation negative pressure in the pleural cavity may cause the water to be lifted slightly up the rigid tube in the water seal but this negative pressure cannot overcome the column height of the tube and the elevation differences between the patient and the bottle. Also, the underwater seal can provide diagnostically relevant information in that if air bubbles are observed leaving the tip of the submerged tube, it is indicative that air is being withdrawn from the pleural cavity.

Another tube communicates between the underwater seal bottle and a suction control bottle. This suction cotnrol bottle is partially filled with water and also includes a second tube in fluid communication with a source of vacuum which provides the suction force for the drainage system. A third rigid control tube communicating between the exterior of the suction control bottle and a point below the water surface. The function of the suction control bottle is to maintain a predetermined subatmospheric pressure in the collecting bottle. Hospital vacuum sources usually produce more vacuum force than is required and the suction control bottle allows outside air to enter the system so that the vacuum forces are reduced to the desired magnitude. By way of example if the physician recommends a suction force of 15 cm of water, the nurse adds water to the bottle until the bottom of the control tube is 15 cm below the water level or, if possible, she adjusts the tube height to achieve the same result. When applied vacuum force exceeds 15 cm of water, outside air is drawn into the suction control bottle through the control tube and exits below the water level, bubbling upwardly out of the water and into the vacuum system, thereby reducing the vacuum force in the suction control bottle and also in the collecting bottle to which it is in fluid communication. It is believed that nurses prefer a suction control bottle as a means for controlling vacuum forces because the observation of a steady stream of air bubbles is a visual indication that the suction control system is operating, and unlike mechanical devices the suction control bottle needs no calibration.

Although a three bottle system contains many of the safeguards and features believed to be preferred by doctors and nurses, it also has deficiencies. These deficiencies include the possibility of breakage, and elaborate set-up procedures involving many components. In addition, there is potential for contamination and spilling when changes are made to the liquid level or tube height in the suction control bottle to change the vacuum forces in the collection bottle. Also, a movable suction control tube projecting out of the top of a suction control bottle is believed to be a deficiency because it can be accidentally moved to produce an unwanted change in the system pressure and the exposed tube is susceptible to contamination.

A chest drainage system of the reduced complexity is taught in U.S. Pat. No. 4,439,190 to Protzmann et al. Protzmann et al. teach a common manifold to which a collection chamber and a suction control chamber are releasably secured, while a water seal chamber is permanently attached thereto. Protzmann et al. teach pressure regulation by the addition or removal of liquid from the system rather than by raising or lowering a rigid tube. The Protzmann et al. apparatus is an improvement over the prior art in that there is apparently less chance of contamination, spilling or inadvertent adjustments of pressure regulation because of the rigid structure and elimination of the pressure regulating tube extending outwardly from the top of the apparatus. However, Protzmann et al. is more difficult to use because pressure changes require the removal of the suction control chamber so that liquid may be added or removed therefrom and the subsequent reattachment of the suction control chamber to the manifold.

Although the above-recited teachings of Protzmann et al. provide improvements over the traditional three bottle system by reducing the complexity of the system and providing a compact simplified structure that appears to be less susceptible to damage during use and more easily moved with the patient, Protzmann et al. still have not overcome some of the deficiencies in the prior art. Most notably, a change in vacuum forces in the collection chamber can still be achieved only by adding or removing fluid from the system. This procedure and the procedure of the aforementioned three bottle system wherein the pressure is changed by raising and lowering a rigid suction control tube within a suction control bottle, or adding or removing liquid, are time consuming procedures which offer potential for contamination, spilling and inadvertent adjustment of the system.

A further improvement is provided in a chest drainage unit sold by the Argyle Division of Sherwood Medical under the trademark name of Sentinel Seal. This device provides for the manual adjustment of vacuum forces within the collection chambers by turning a dial position on the top surface of the unit. A manometer is provided to indicate the magnitude of the vacuum forces within the collection chamber. There is less potential for spilling or contamination with the Argyle apparatus because pressure can be easily changed by rotating a dial without adding or removing fluid, or moving a rigid tube projecting outwardly from the top of the unit. To assure that the desired pressure is provided within the suction unit a manometer is provided. It is believed that this is a more costly apparatus because it requires a more complex mechanical regulator assembly and a manometer means. Although the Argyle apparatus greatly simplifies the procedure for varying vacuum forces within the collection chamber, it does not provide the desired visual indication, i.e., the bubble stream which indicates that the suction control system is operating.

Although the prior art provides various improvements over chest drainage systems having individual bottles interconnected by tubing, there is still a need for a simple, straightforward, easily fabricated chest drainage apparatus which provides visual indicia of suction control regulator operability along with means for easily changing the vacuum forces within the collection chamber without having to add or remove liquid from the system or without having to adjust the position of a rigid open movable tube projecting from the system.

SUMMARY OF THE INVENTION

The operable drainage apparatus of the present invention for draining fluid from a mammalian body cabity includes a collection chamber for collecting the fluid having inlet means in fluid communication with the collection chamber for receiving fluid from the body cavity. One-way valve means is in fluid communication with the collection chamber for preventing air from entering the body cavity from the inlet means. A vacuum control chamber has a closed lower end and an upper end in fluid communication with the one-way valve means. A flexible conduit has as first end in fluid communication with the exterior of the drainage apparatus and a second end movably positioned within the vacuum control chamber. Elevation adjustment means is connected to the flexible conduit for moving the second end of the flexible conduit upwardly and downwardly to various positions within the vacuum control chamber. Suction outlet means in fluid communication with the vacuum control chamber is provided for communicating with a source of vacuum.

In accordance, with another embodiment of the present invention, an operable chest drainage apparatus for draining fluid from the pleural cavity of a surgical patient includes a collection chamber for collecting the fluid having as inlet port in fluid communication with the collection chamber adapted to receive fluid from the patient. An underwater seal chamber in fluid communication with the collection chamber is provided for preventing air from entering the patient from the inlet port. An elongate partially transparent vacuum control chamber has a closed lower end and upper end in fluid communication with the underwater seal chamber. A flexible conduit has a first end in fluid communication with the exterior of the chest drainage apparatus and a second end movably positioned within the vacuum control chamber. Elevation adjustment means connected to the flexible conduit is provided for moving the second end of the flexible conduit upwardly and downwardly to various positions within the vacuum control chamber. The elevation adjusted means is manually activatable from the exterior of the chest drainage apparatus. A suction outlet port is in fluid communication with the upper end of the vacuum control chamber for communicating with a source of vacuum. A quantity of liquid is provided in the vacuum control chamber, covering the second end of the flexible conduit so that the second end can be adjusted upwardly and downwardly within the liquid for varying the vacuum forces in the collection chamber when the suction outlet port is communicating with a source of vacuum. Measuring indicia on the vacuum control chamber is positioned so that the user can determine the distance the second end of the flexible conduit is below the free upper surface of the liquid.

A number of advantages and objectives are attained consistent with the principles of the present invention. Primarily, the present invention provides a simple, straightforward, easily fabricated chest drainage apparatus which provides visual indicia of suction control regulation operability along with means for easily changing the vacuum forces within the collection chamber without having to add or remove liquid from the system or without having to adjust the position a rigid open movable tube projecting from the top of the system.

BRIEF DESCRIPTION OF THE DRAWINGS

FIG. 4 is a right side elevation view of the preferred chest drainage apparatus;

FIG. 5 is a left side elevation view of the preferred chest drainage apparatus;

DETAILED DESCRIPTION

Figure 1:
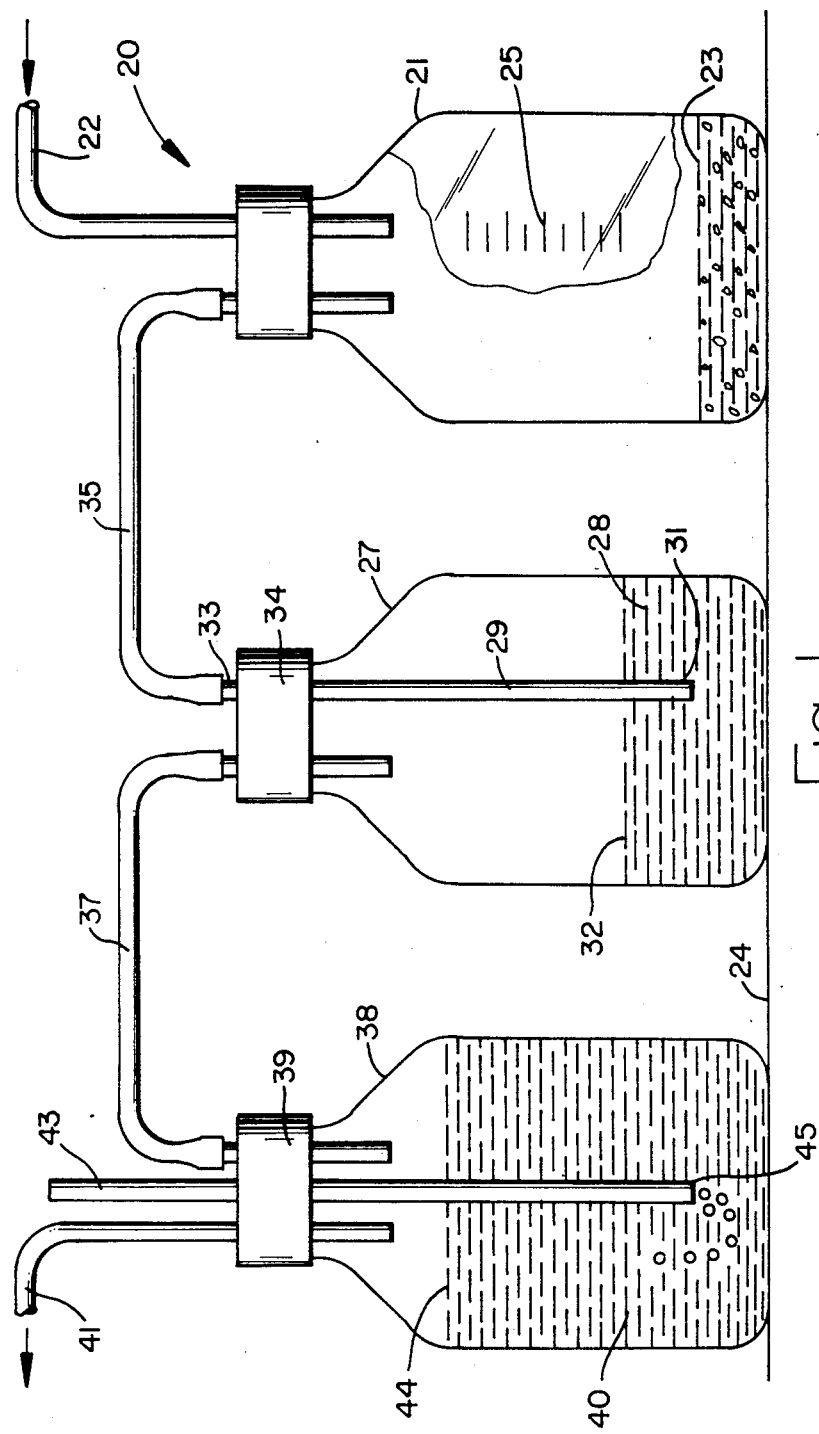
FIG. 1 is a side elevation view of a prior art three-bottle chest drainage system.
Figure 2:
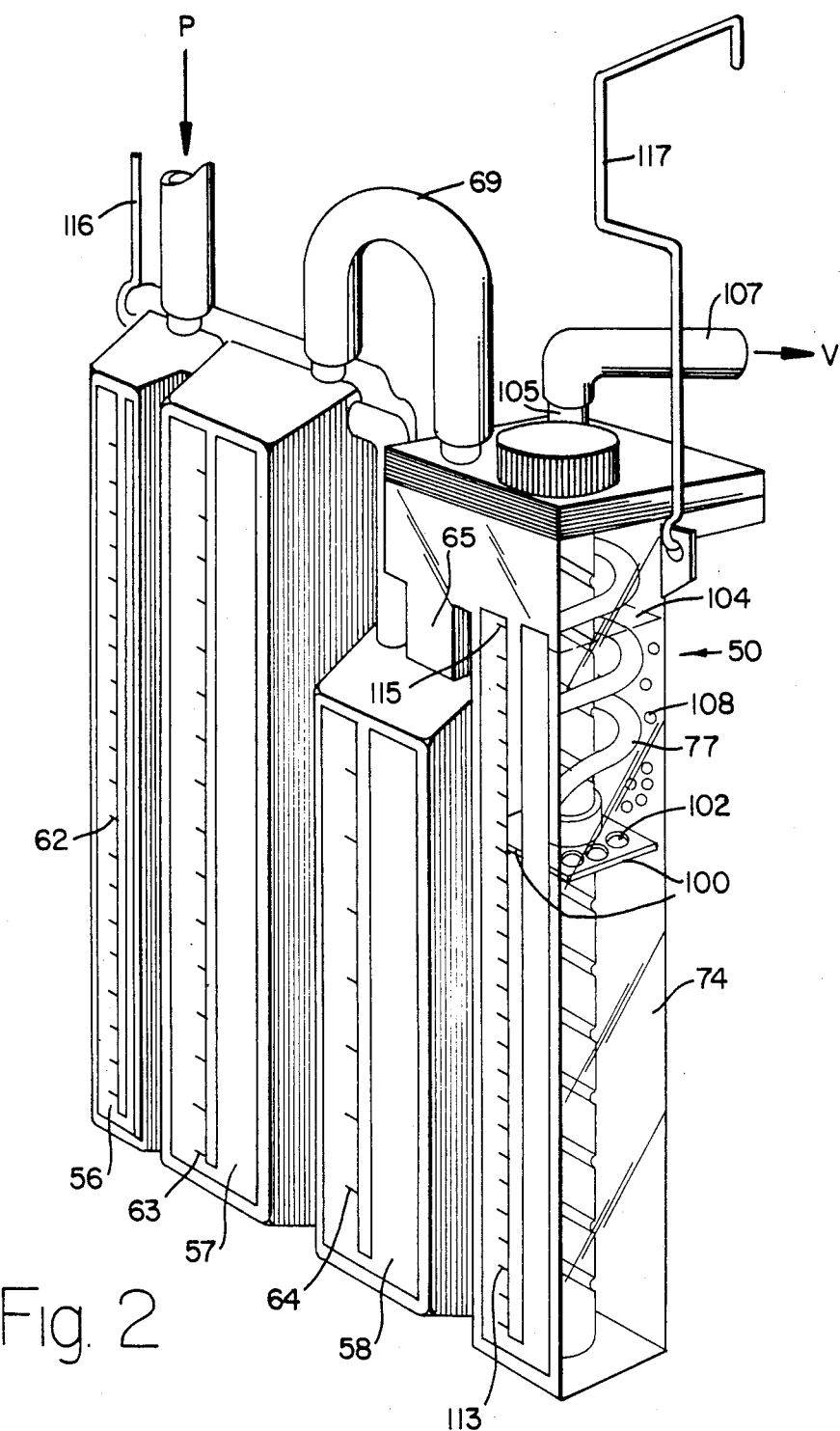
FIG. 2 is a perspective view of the preferred chest drainage apparatus of the present invention.
Figure 3:
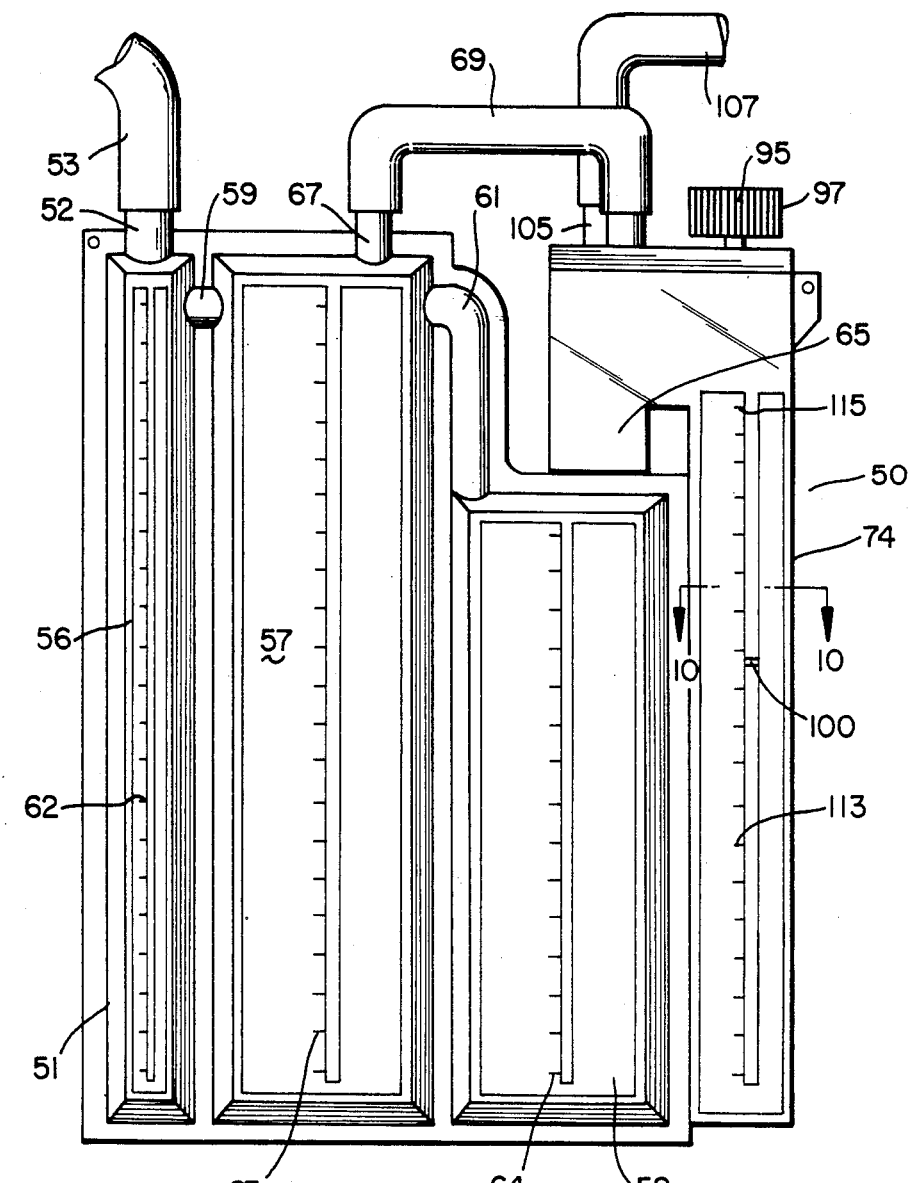
FIG. 3 is a front elevation view of the preferred chest drainage apparatus.
Figure 7:
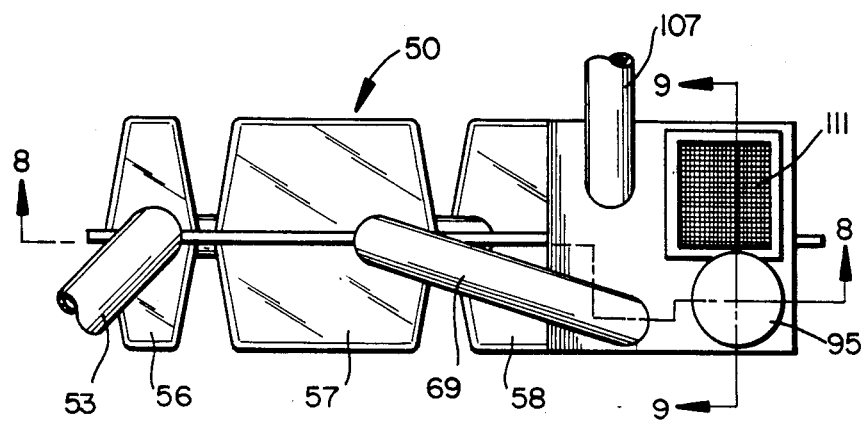
FIG. 7 is a top plan view of the preferred chest drainage apparatus.
Figure 6:
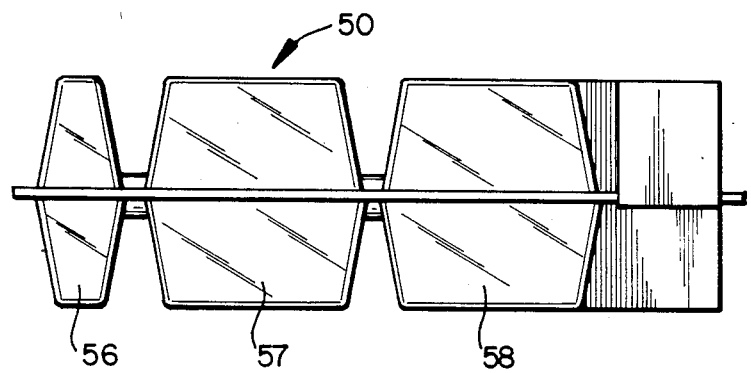
FIG. 6 is a bottom plan view of a preferred chest drainage apparatus.
Figure 8:
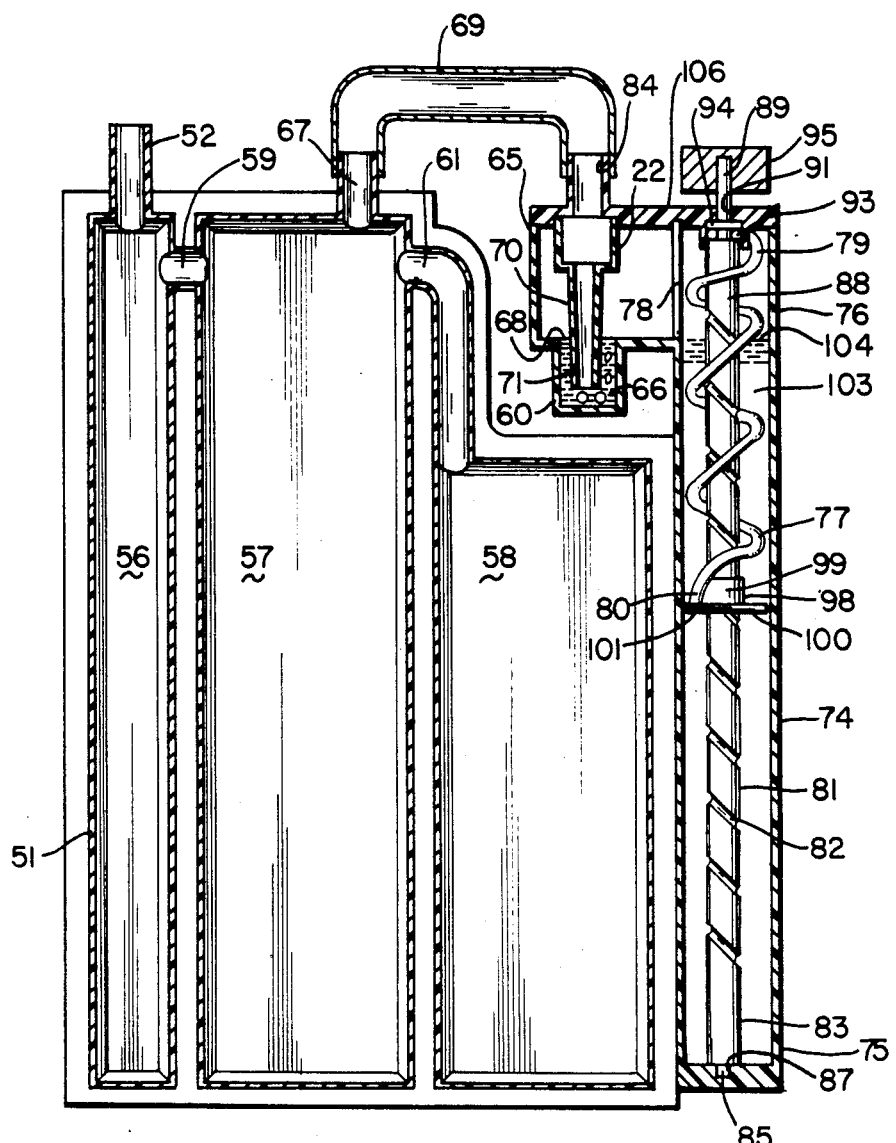
FIG. 8 is a cross-sectional view of the chest drainage apparatus of FIG. 7 taken along line 8—8.

While this invention is satisfied by embodiments in many different forms, there is shown in the drawings and will herein be described in detail preferred embodiments of the invention with the understanding that the present disclosure is to be considered as exemplary of the principles of the invention and is not intended to limit the invention to the embodiments illustrated. The scope of the invention will be measured by the appended claims and their equivalents.

Adverting now to FIG. 1, a known prior art three-bottle chest drainage apparatus 20, for draining fluid from the pleural cavity of a surgical patient, includes the collection bottle 21, resting on a work surface 24, in fluid communication with the patient's pleural cavity via tube 22. The collection bottle contains fluid 23 collected from the patient's pleural cavity and includes graduations 25 so that the user can determine the volume of fluid collected. An underwater seal bottle 27 contains a quantity of liquid 28, such as water, and a rigid tube 29 having a lower end 31 positioned below the free upper surface 32 of water 28, and an upper end 33 passing through stopper 34 and in fluid communication with the collection bottle through tube 35. The underwater seal bottle does not interfere with the drainage of liquid and gas from the pleural cavity, but it functions as a one-way valve to prevent air from passing through lower end 31, through tube 29 and reentering the patient's pleural cavity. In operation, negative pressure in the pleural cavity may cause water to be lifted slightly upwardly into rigid tube 29, above free upper surface 32 of water 28, however, this negative pressure usually cannot overcome the column height of tube 29 and the elevation differences between the patient and the bottles which are usually positioned below the patient. Also, the water seal can provide diagnostically relevant information in that if gas bubbles are observed leaving lower end 31 of tube 29, it is indicative that gas is being withdrawn from the pleural cavity.

A tube 37 communicates between the underwater seal bottle and a suction control bottle 38 through a stopper 39 therein. The suction control bottle is partially filled with liquid 40, such as water. A suction tube 41 is in fluid communication with the source of vacuum, which provides a suction force for the drainage system. A rigid vacuum control tube 43 communicates between the exterior of the suction control bottle and a point below free upper surface 44 of water 40. The function of the suction control bottle is to maintain a predetermined subatmospheric pressure in collection bottle 21. Hospital vacuum sources usually produce more vacuum force than is required and the suction control bottle allows outside air to enter the suction control bottle through tube 43, so that the vacuum forces in the collection bottle are reduced by this outside air which is introduced into the system. By way of example, if a physician recommends a suction force of 15 cm of water, the nurse adds water to the bottle until the lower end 45 of vacuum control tube 43 is 15 cm below free upper surface 44 of the water or, if possible, the nurse adjusts the height of tube 43 manually, from the outside of the suction control bottle to achieve the same result. When the applied vacuum force exceeds 15 cm of water, outside air is drawn into suction control bottle 38 through vacuum control tube 43 and exits at lower end 45, bubbling upwardly out of the water and into the vacuum system, thereby reducing the vacuum force in the suction control bottle and also in the collecting bottle to which it is in fluid communication. As recited hereinabove, the three-bottle system has deficiencies in that there is the possiblility of breakage during use and there are elaborate set up procedures involving many components. Also, there is a potential for contamination and spilling when changes are made to the liquid level or tube height in the suction control bottle to change the vacuum forces in the collection bottle.

Referring now to FIGS. 2–10, wherein the preferred embodiment of the present invention is illustrated, an operable chest drainage apparatus 50 for draining fluid from the pleural cavity of a surgical patient includes a collection chamber 51 for collecting the fluid. An inlet port 52 is in fluid communication with the collection chamber and adapted to receive fluid from the patient through a flexible tube 53. In this preferred embodiment collection chamber 51 includes separate receptacles 56, 57 and 59 all in fluid communication with each other and with inlet port 52. Receptacle 56 is in fluid connunication with receptacle 57 through conduit 59 and receptacle 57 is in fluid communication with receptacle 58 through conduit 61. Receptacles 56, 57 and 58 are serially arranged so that when one of the receptacles is filled with fluid collected from the patient, additional collected fluid will overflow therefrom to fill the next receptacle and so on until all receptacles are full. It is preferred that the volume of the receptacles be such that in the majority of all applications the therapy will be completed before all three receptacles are filled with fluid collected from the patient.

Volume measuring indicia, in the form of graduations 62 on the exterior of receptacle 56, allows the nurse to determine the volume of fluid collected in the receptacle by observing the relative position of the upper surface of the collected fluid in receptacle 56 and the graduations. When receptacle 56 is full of collected fluid, excess fluid flows through conduit 59 into receptacle 57. Further, when receptacle 57 is full of fluid collected from the patient, excess fluid flows through conduit 61 into receptacle 58. Receptacles 57 and 58 have graduations 63 and 64, respectively, for measuring the volume of fluid collected. It is preferred that the graduations are numbered consecutively so that only one reading is required to determine the total fluid volume collected. For example, if receptacle 58 is partially full of collected fluid, graduations 64 corresponding with the fluid level should indicate the combined volume of receptacles 56 and 57 plus that portion of receptacle 58 which contains fluid. It is preferred that the volume of all three receptacles be apparoximately 2000 ml. It is also preferred that the first receptacle have the smallest cross sectional area so that it will provide the most accurate measurement of the volume of fluid collected by virtue of the fact that the free upper surface of the collected liquid will change more with respect to the volume collected than in the other larger receptacles.

An underwater seal chamber 65 is in fluid communication with collection chamber 51 through conduit 67 in the collection chamber, conduit 84 of the underwater seal and flexible tube 69. Accordingly, underwater seal chamber is also in fluid communication with the patient's pleural cavity through inlet port 52. Underwater seal chamber 65 includes a lower reservoir portion 60 and an underwater seal tube 70 having a lower end 71 positioned in reservoir portion 60 below free upper surface 68 of liquid 66, such as water, so that air passing from the collection chamber toward the source of vacuum will flow through conduit 84, tube 70 and exit from lower end 71 in the form of air bubbles through the liquid. It is preferred that lower end 71 of the tube 70 be positioned approximately about two cm below free upper surface 68 of the liquid. Accordingly, the underwater seal does not interfere with the drainage of liquid from the patient. The underwater seal chamber functions as a one-way valve, or more specifically an underwater seal, to prevent air from reentering the pleural cavity through the submerged lower end 71 of tube 70. In operation, negative pressure in the pleural cavity may cause liquid 66 to be lifted upwardly in underwater seal tube 70 but this negative pressure cannot overcome the column height of the tube and the elevation differences between the patient and of the chest drainage apparatus of the present invention which should preferably be positioned below the patient's pleural cavity when in use.

Enlarged upper end portion 72 of underwater seal tube 70 is provided to act as a reservoir during times of momentary vacuum inbalance which tends to draw liquid up the underwater seal and then into flexible tube 69. If this liquid is drawn into flexible tube 69 and into the reservoir, after the momentary inbalance pressure there may not be enough liquid remaining for the underwater seal to function properly. Enlarged upper end portion 72 acts as a reservoir to prevent fluid from being drawn out of the underwater seal into the collection chamber through tube 69. It may also be desirable to provide a float type valve (not shown) in enlarged upper end portion 72 which would seal aperture 84 when water enters the enlarged upper end portion 72 thus assuring that no watr will be drawn from the underwater seal into the collection chamber.

As with the prior art underwater seal bottle, the underwater seal chamber of the present invention can provide diagnostically relevant information in that if gas bubbles are observed leaving tip 71 of tube 70, it is indicative that gas is being withdrawn from the patient's pleural cavity. As will also be explained in more detail hereinafter upper portion 73 of underwater seal chamber 65 is in fluid communication with a source of vacuum.

An elongate preferably partially transparent vacuum control chamber 74 includes a closed lower end 75 and an upper end 76 in fluid communication with underwater seal chamber 65 through opening 78. A flexible conduit or tube 77 includes a first end 79 in fluid communication with the exterior of the chest drainage apparatus and a second end 80 movably positioned within vacuum control chamber 74.

An elevation adjustment means is provided for moving second end 80 upwardly and downwardly to various positions within vacuum control chamber 74. The elevation adjustment means includes a lead screw or vacuum control shaft 81 having an externally positioned screw thread 82 on the surface thereof. A lower or distal end 83 of vacuum control shaft 81 includes a reduced diameter projection 85 positioned within a recessed 87 in closed lower end 75 so that it is contained therein but free to rotate. An upper or proximal end 88 of the vacuum control shaft has a reduced diameter portion 89 which passes through a bore 91 in upper end 76 of the vacuum control chamber so that lead screw 81 is free to rotate. It is preferred that the clearance between bore 91 and upper reduced diameter portion 89, and the clearance between reduced diameter projection 85 and blind recess 87 be held resonably tightly so that lead screw 81 will be able to rotate freely but be held in a controlled upright position with the vacuum control chamber.

Upper end 76 of the vacuum control chamber also includes annular flange 92 projecting downwardly therefrom. A resilient sealing ring 93, such as the known O-ring, is positioned over reduced diameter portion 89 and held in position by a collar 94. Sealing ring 93 cooperating with annular flange 92 and reduced diameter projection 89 provides a reasonably airtight seal so that gases cannot readily enter or leave the vacuum control chamber through bore 91. It will be apparent to one skilled in the art that numerous constructions can be used to seal an interface between a bore and a rotatable member and that the arrangement using a resilient sealing ring, described hereinabove, is exemplary of these many possibilities. A knob 95 is attached to the upper end of the vacuum control shaft. Knob 95 includes a circular knurled outer surface 97 to facilitate turning the knob which in turn rotates the vacuum control shaft.

A shaft follower 98 includes a sleeve portion 99 and a platform portion 100 at the lower end of the sleeve portion. The inside diameter of sleeve portion 99 contains inwardly projecting screw thread (not shown) movably engaging screw thread 82 of the vacuum control shaft. Platform portion 100, as viewed along the longitudinal axis of the vacuum control shaft, is rectangularly shaped and smaller than the inside cross sectional shape of the vacuum control chamber so that the platform is free to move up and down the vacuum control chamber along the vacuum control shaft, however, platform 100 will not rotate within the vacuum control chamber because of its rectangular shape. Accordingly, vacuum control shaft 81 may be manually rotated by turning knob 95 causing shaft follower 98 to travel upwardly and downwardly along the shaft depending upon the direction of rotation of the shaft. It will be apparent to one skilled in the art that there are numerous cooperating structures which can be used for movably engaging the vacuum control shaft and the shaft follower so that rotation of the shaft will cause the follower to move along the shaft and that the arrangement described hereinabove is exemplary of these many possibilities. Also, it is within the purview of this invention to include a follower having one or more spherically shaped inwardly directed projections which ride in the threads of the threaded shaft, or a shaft having outwardly projecting thread cooperating with a follower having a mating inwardly directed engaging thread, or a shaft and follower combinations having multiple threads, ball bearing type followers and the like.

In this preferred embodiment platform portion 100 of the shaft follower includes aperture 101 having second end 80 of flexible conduit 77 fixedly positioned therein so that the second end of flexible conduit 77 moves upwardly and downwardly within the vacuum control chamber as vacuum control shaft 81 is rotated. The quantity of liquid such as water or saline solution 103 is contained within the vacuum control chamber and the underwater seal chamber 65. By rotating knob 95, the user can change the distance between free upper surface 104 of the liquid and second end 80 of the flexible conduit. As will be explained in more detail hereinafter the ability to move the second end of the flexible tube to various positions with respect to the free upper surface of the water is an important feature of the instant invention.

A suction outlet port 105 projects outwardly from upper wall 106 of underwater seal chamber 65 so that said port is in fluid communication with the underwater seal chamber and with the vacuum control chamber. The suction outlet port can also be positioned in the upper wall of the vacuum control chamber because both the underwater seal and the vacuum control chamber are in fluid communication with each other. Suction outlet port 105 is provided for establishing fluid communication between the vacuum control chamber and a source of vacuum. In use, a flexible tube 107 is utilized to connect the outlet port with a source of vacuum V.

Figure 9:
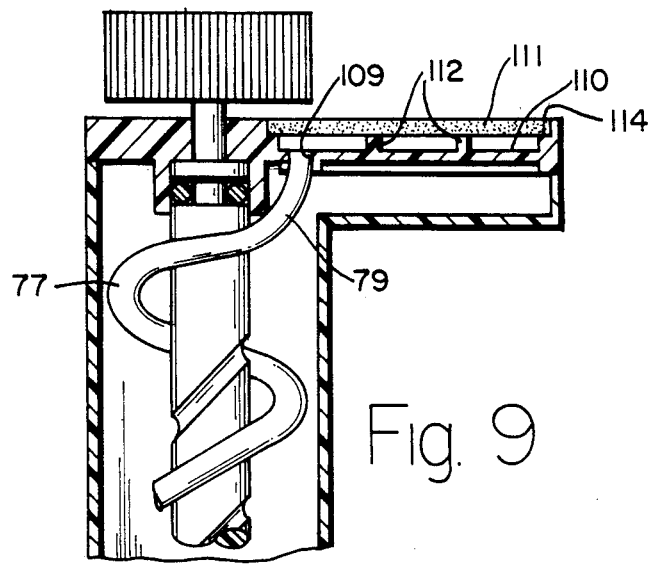
FIG. 9 is a partial cross-sectional view of the chest drainage apparatus of FIG. 7 taken along line 9—9.
Figure 10:
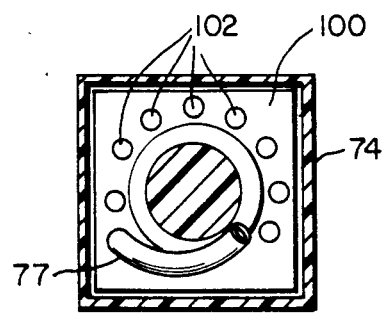
FIG. 10 is a cross-sectional view of the chest drainage apparatus of FIG. 3 taken along line 10—10.

As best illustrated in FIG. 9, first end 79 of flexible conduit 77 is fixedly positioned in aperture 109 in the vacuum control chamber so that the first end is in fluid communication with the outside of the chest drainage apparatus through filter housing 110 and air filter element 111. In this preferred embodiment air filter 111 is a thin membrane type filter which is heat sealed to sealing ledge 114, which runs around the periphery of the filter housing, in a preferably airtight arrangement. Filter element 111 lies within a single suction path extending from the interior of the flexible conduit 77 to the exterior of the chest drainage apparatus so that all gases exchanged from the vacuum control chamber through conduit 77 and the outside of the chest drainage apparatus pass through filter element 111. It is preferable that the filter element have a maximum pore rating of about 0.5 micron so that it acts as a substantial barrier for particles including microorganisms, which are about 0.5 micron and larger. Supporting ribs 112 are provided to support the filter element and to prevent it from collapsing over aperture 109.

It is also desirable to provide an aperture (not shown) in the upper portion of vacuum control chamber 74 or in some portion of the chest drainage apparatus above the free upper surface of the liquid and to seal this aperture with a one-way valve (not shown) which remains in a closed position while the interior of the vacuum control chamber is exposed to subatmospheric pressures. In the event that the interior of the vacuum control chamber is exposed to pressures in excess of atmospheric pressure the valve should open and relieve the pressure therein. This valve is primarily for acting as a safety valve to protect the patient from harm if, for example, flexible tube 107 is inadvertently connected to a source of pressure rather than a source of vacuum.

Vacuum control chamber 74 also includes graduations 113 for indicating the distance between free upper surface 104 of liquid 103 and platform portion 100 of the shaft follower so that the user may determine the distance between the free upper surface of the water and second end 80 of the flexible conduit which, as will be explained in detail hereinafter, determines the vacuum force in the collection chamber.

It is preferred that the chest drainage apparatus of the present invention be sterile when used and provided in a sterile overwrap (not shown). In use, the nurse removes the sterile overwrap. At this time, liquid such as sterile water or saline solution such as 0.9% saline solution, provided with the chest drainage apparatus, or obtained separately, is poured into the apparatus through suction outlet port 105 until the liquid level in the vacuum control chamber reaches the fill line 115 which is the zero position on graduations 113. At this point, the level of liquid 103 in the vacuum control chamber will be approximately 24 cm deep and the level of liquid in the underwater seal chamber will be high enough so that approximately two cm of underwater seal tube is positioned below free upper surface 68 of the liquid in the underwater seal chamber. It should be noted that, in this preferred embodiment the vacuum control chamber and the underwater seal chamber are positioned so that both can be filled simultaneously by pouring the liquid through the suction outlet port so that free upper surface 68 of the liquid in the underwater seal chamber is substantially at the same height as free upper surface 104 of the liquid in the vacuum control chamber. Suction outlet port 105 is now connected to a suitable vacuum source using flexible tube 107. The chest drainage apparatus should now be placed at a level below the level of the patient by using a floor stand (not shown) or hangers 116 and 117, as illustrated in FIG. 1.

The exact suction force prescribed by the attending physician can be set by turning knob 95 in a counterclockwise or clockwise direction to raise or lower second end 80 of flexible conduit 77, as indicated by comparing the position of platform 100 to graduations 113 until platform 100 is aligned with the specific vacuum level prescribed by the physician as indicated by graduations 113. For example, if the physician prescribes a vacuum level of 15 cm of water, the knob should be turned until platform 100 is adjacent to the 15 cm graduation on the vacuum control chamber. The source of vacuum may now be activated.

The chest drainage apparatus may now be connected to the surgical patient P through inlet port 52 with flexible tube 53 using accepted sterile technique. Fluid collected from the patient will flow directly into receptacle 56 wherein the volume of fluid collected can be determined by comparing the free upper surface of the collected fluid with graduations 62. When receptacle 56 is full of collected fluid, excess fluid flows through conduit 59 into receptacle 57, and then into receptacle 58, when receptacle 57 is full.

The magnitude of the vacuum forces within the collection chamber may be changed during the drainage procedure simply by adjusting knob 95 to obtain the desired vacuum force as evidenced by the relative position of platform 100 in the vacuum control chamber to the free upper surface of the liquid. Further, when suction forces developed in the external suction system exceed the preset suction force, environmental air will be drawn through filter element 111, through first end 79 of the flexible conduit and out of second end 80 into liquid 103 where it will bubble upwardly through the liquid and pass into the suction opening toward the source of vacuum V, thus lowering the effective vacuum within the chest drainage apparatus. As the outside air bleeds through flexible conduit 77, bubbles of air 108 in the water will provide evidence to the attending nurse that the system is operational and that the applied vacuum force is in excess of the desired vacuum force. Additional apertures 102 are provided in platform portion 100 so that the air bubbles will pass freely upwardly, through apertures 102, to the suction outlet port. In the preferred embodiment, air filter element 111 is capable of filtering particulate matter and bacteria so that the air entering the system is sterile and will not contaminate liquid 103. It is also preferred that the side portion of vacuum control chamber 74 is transparent so that the bubbles of air emanating from the flexible conduit will be readily visible.

Figure 11:
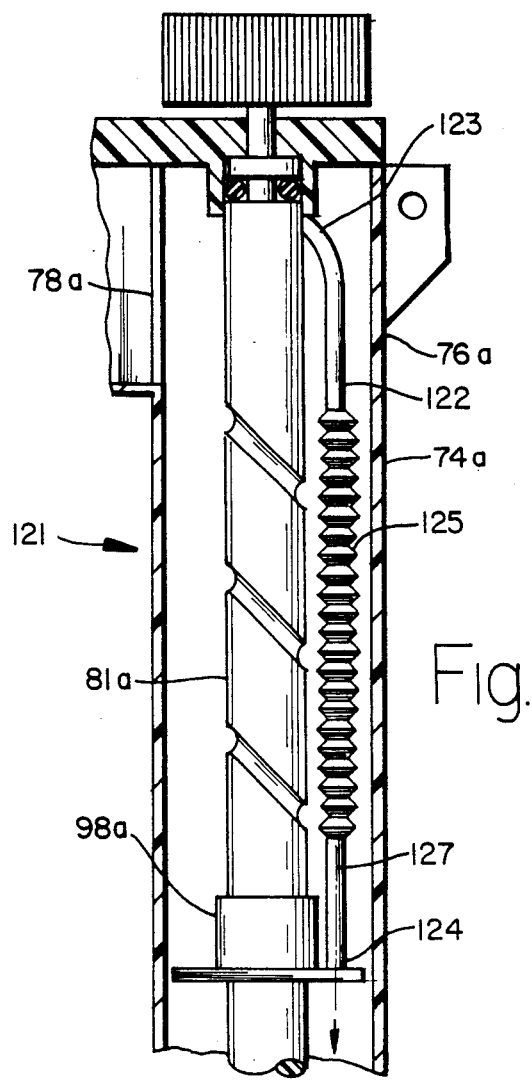
FIG. 11 is a partial cross-sectional view of an alternative chest drainage apparatus of the present invention.

Referring now to FIG. 11 an alternative chest drainage apparatus 121 of the instant invention includes components which are substantially identical to the components of the embodiment of FIGS. 2-10. Accordingly, similar components performing similar functions will be numbered identically to those components in the embodiments of FIGS. 2-10, except that a suffix "a" will be used to identify these components in FIG. 11. This alternative operable chest drainage apparatus includes a vacuum control chamber 74a having a closed lower end (not shown) and upper end 76a in fluid communication with an underwater seal chamber (not shown) through opening 78a. A flexible conduit 122 includes a first end 123 in fluid communication with the exterior of the chest drainage apparatus and a second end 124 movably positioned within the vacuum control chamber. Flexible conduit 122 also includes a bellows shaped portion 125 capable of expanding and contracting along its longitudinal axis 127 as a shaft follower 98a moves upwardly and downwardly along a vacuum control shaft 81a. In this embodiment it is not necessary to coil the flexible conduit around the vacuum control shaft as in the embodiment of FIGS. 2-10, so that a smaller cross section vacuum control chamber may be used thus saving material and reducing the amount of liquid required to fill the vacuum control chamber.

It is also within the purview of the present invention to include an embodiment wherein the bellows shaped flexible conduit is larger than the vacuum control shaft so that the shaft may be positioned within the bellows shaped portion of the conduit rather than adjacent to it. In this embodiment (not shown) a portion of the vacuum control shaft would be within the bellows-shaped portion of the conduit, preferably with the vacuum control shaft concentrically positioned within the bellows shaped portion of the conduit, so that air passing through the flexible conduit passes through the space defined by the inside of the bellows shaped portion and the outside of that portion of the vacuum control shaft that is within the bellows shaped portion. In this embodiment, the second or lower end of the flexible conduit can be connected to the platform of the shaft follower with an aperture or apertures for the flow of outside air from the conduit being positioned in the platform within the periphery of the inside of the conduit, and additional venting apertures being positioned outside of the periphery of the conduit. The upper end of the conduit can be connected to the upper wall of the vacuum control chamber with an appropriate aperture in this wall to allow fluid communication with the exterior of the apparatus, preferably, through an air filter.

It is also within the purview of the present invention to include means other than a rotatable shaft and a shaft follower for moving the second end of the flexible conduit upwardly and downwardly within the vacuum control chamber. For example, the vacuum control chamber can be constructed to slidably engage an externally positioned magnet. This magnet could be moved upwardly and downwardly along the exterior of the vacuum control chamber. The second end of the flexible conduit could be held by a follower made of material responsive to the magnet so that movement of the magnet will cause movement of the second end of the flexible conduit.

A wide variety of rigid materials are suitable for constructing the collection chamber, underwater seal chamber and vacuum control chamber, however, thermoplastic material such as SAN (stryene-acrylonitrile), polystyrene, polycarbonate and acrylic are preferred. A wide variety of flexible materials are suitable for forming the flexible conduit for use in the vacuum control chamber with plastic materials such as polyurethane, silicone and polyvinylchloride being preferred. Numerous commercially available filter materials are suitable for the air filter elements however filter elements made of nonwoven thermoplastic are desirable and filter elements having inherently good heat sealing properties are preferred. Certain membrane filters available from W. L. Gore and Associates, Inc. of Elkton, MD, and sold as GORE-TEX Membrane Products are suitable for use in the air filter element.

Thus, it can be seen that present invention provides a simple, straightforward, easily fabricated chest drainage apparatus which provides visual indicia of suction control regulation operability along with a means for easily changing the vacuum forces within the collection chamber without having to add or remove liquid from the system or without having to adjust the position of a rigid movable tube projecting from the top portion of the system. The present invention also provides a filter means to protect the liquid in the vacuum control chamber from certain particulate matter and airborne microorganisms in the environment.

What is claimed is:

1. An operable chest drainage apparatus for draining fluid from the pleural cavity of a surgical patient comprising:
    a collection chamber for collecting the fluid;
    inlet means in fluid communication with said collection chamber for receiving fluid from the patient;
    one-way valve means in fluid communication with said collection chamber for preventing air from entering the patient from said inlet means;
    an elongate vacuum control chamber having a closed lower end and an upper end in fluid communication with said one-way valve means;
    a flexible conduit having a fixedly positioned first end in fluid communication with a fixed opening to the atmosphere and with the exterior of said apparatus and a second end movably positioned within said vacuum control chamber;
    variable elevation adjustment means connected to said flexible conduit for vertically moving said second end upwardly and downwardly to various positions within said vacuum control chamber, the distance between said second end and said first end being decreased as said second end moves upwardly and increased as said second end moves downwardly, said elevation adjustment means being activatable from the exterior of said apparatus; and
    suction outlet means in fluid communication with said vacuum control chamber for communicating with a source of vacuum.

2. The chest drainage apparatus of claim 1 further including a quantity of liquid in said vacuum control chamber covering said second end of said flexible conduit so that said second end can be adjusted upwardly and downwardly within said liquid for varying the vacuum forces in said collection chamber when said suction outlet means is communicating with a source of vacuum.

3. The chest drainage apparatus of claim 2 wherein said liquid is selected from the group consisting of water and an saline solution.

4. The chest drainage apparatus of claim 2 wherein a portion of said vacuum control chamber is transparent and said vacuum control chamber includes measuring indicia positioned so that the user can determine distances said second end of said flexible conduit is below the free upper surface of said liquid.

5. The chest drainage apparatus of claim 1 wherein said one-way valve means includes an underwater seal chamber having a reservoir portion and underwater seal tube, said tube having a lower tube end positioned within said reservoir and an upper tube end in fluid communication with said vacuum control chamber.

6. The chest drainage apparatus of claim 4 further including a quantity of liquid in said reservoir portion of underwater seal chamber contacting said lower tube end.

7. The chest drainage apparatus of claim 1 wherein a portion of said vacuum control chamber is transparent so that said second end of said flexible conduit is visible therethrough.

8. The chest drainage apparatus of claim 1 wherein said elevation adjusting means includes: a vacuum control shaft formed with threadable engaging means on the exterior surface thereof, said shaft being positioned in said vacuum control chamber so that a distal end of said shaft is resting in said closed lower end and a proximal end of said shaft passes through said upper end in an airtight arrangement so that said shaft may be rotated by manually turning said proximal end; a shaft follower having a side wall portion formed with mating threadable engaging means engaging said shaft, said follower being in slidable engagement with said vacuum control chamber so that rotation of said shaft causes said follower to travel upwardly and downwardly along said shaft; and conduit engaging means for holding said conduit in a fixed position relative to said follower so that said second end of said conduit moves upwardly and downwardly within said vacuum control chamber as said shaft is rotated.

9. The chest drainage apparatus of claim 8 wherein said flexible conduit includes a bellows shaped portion positioned so that said conduit can expand and contract along its longitudinal axis, said vacuum control shaft being positioned so that a portion of said vacuum control shaft is within said bellows shaped portion wherein air passing through said flexible conduit passes through the space defined by the inside of said bellows shaped portion and the outside of the portion of said vacuum control shaft within said bellows shaped portion.

10. The chest drainage apparatus of claim 1 wherein said flexible conduit has a circularly shaped cross section.

11. The chest drainage apparatus of claim 1 wherein said flexible conduit includes a bellows shaped portion so that said conduit can expand and contract along its longitudinal axis.

12. The chest drainage apparatus of claim 1 wherein said collection chamber includes a plurality of separate receptacles all in fluid communication with each other and with said inlet means and said one-way valve means, said receptables being serially arranged so that when one of said receptacles is filled with fluid collected from the patient, additional collected fluid will overflow therefrom to fill the next receptacle and so on until all receptacles are full.

13. The chest drainage apparatus of claim 1 further including a filter means positioned so that all gases passing through said first end of said flexible conduit must pass through said filter means.

14. The chest drainage apparatus of claim 13 wherein said filter means includes a porous filter element having a maximum pore rating of about 0.5 micron for filtering particulate matter including microorganisms from gas passing therethrough.

15. The chest drainage apparatus of claim 1 wherein said collection chamber, said one-way valve means and said vacuum control chamber are made of rigid plastic material.

16. The chest drainage apparatus of claim 15 wherein said plastic material is selected from the group consisting of styrene-acrylonitrile, polystyrene, polycarbonate and acrylic.

17. The chest drainage apparatus of claim 1 wherein said flexible conduit is made of plastic material.

18. The chest drainage unit of claim 16 wherein said plastic material is selected from the group consisting of polyurethane, silicon and vinyl.

19. An operable drainage apparatus for draining fluid from a mammalian body cavity comprising:
a collection chamber for collecting the fluid;
inlet means in fluid communication with said collection chamber for receiving fluid from the body cavity;
one-way valve means in fluid communication with said collection chamber for preventing air from entering the body cavity from said inlet means;
a vacuum control chamber having a closed lower end and an upper end in fluid communication with said one-way valve means;
a flexible conduit having a fixedly positioned first end in fluid communication with a fixed opening to the atmosphere and with the exterior of said apparatus and a second end movably positioned within said vacuum control chamber;
variable elevation adjustment means connected to said flexible conduit for vertically moving said second end upwardly and downwardly to various positions within said vacuum control chamber, the distance between said second end and said first end being decreased as said second end moves upwardly and increased as said second end moves downwardly; and
suction outlet means in fluid communication with said vacuum control chamber for communicating with a source of vacuum.

20. An operable chest drainage apparatus for draining fluid from the pleural cavity of a surgical patient comprising:
a collection chamber for collecting the fluid;
an inlet port in fluid communication with said collection chamber adapted to receive fluid from the patient;
underwater seal means in fluid communication with said collection chamber for preventing air from entering the patient from said inlet port;
an elongate partially transparent vacuum control chamber having a closed lower end and an upper end in fluid communication with said underwater seal means;
a flexible conduit having a fixedly positioned first end in fluid communiction with a fixed opening to the atmosphere and with the exterior of said apparatus and a second end movably positioned within said vacuum control chamber;
vertically elevation adjustment means connected to said flexible conduit for vertically moving said second end upwardly and downwardly to various positions within said vacuum control chamber, the distance between said second end and said first end being decreased as said second end moves upwardly and increased as said second end moves downwardly, said elevation adjustment means being manually activatable from the exterior of said apparatus;
a suction outlet port in fluid communication with said upper end of said vacuum control chamber for communicating with a source of vacuum;
a quantity of liquid in said vacuum control chamber covering said second end of said flexible conduit so that said second end can be adjusted upwardly and downwardly within said liquid for varying the vacuum forces in said collection chamber when said suction outlet port is communicating with a source of vacuum; and
measuring indicia on said vacuum control chamber positioned so that the user can determine the distance said second end of said flexible conduit is below the free upper surface of said liquid.

21. The chest drainage apparatus of claim 20 wherein said elvation adjusting means includes: a vacuum control shaft formed with threadable engaging means on the exterior surface thereof, said shaft being positioned in said vacuum control chamber so that a distal end of said shaft is resting in said closed lower end and a proximal end of said shaft passes through said upper end in an airtight arrangement so that said shaft may be rotated by manually turning said proximal end; a shaft follower having a side wall portion formed with mating threadable engaging means engaging said shaft, said follower being in slidable engagement with said vacuum control chamber so that rotation of said shaft causes said follower to travel upwardly and downwardly along said shaft; and conduit engaging means for holding said conduit in a fixed position relative to said follower so that said second end of said conduit moves upwardly and downwardly within said vacuum control chamber as said shaft is rotated.

22. The chest drainage apparatus of claim 20 wherein said collection chamber includes a plurality of separate receptacles all in fluid communication with each other and with said inlet port and said underwater seal means, said receptacles being serially arranged so that when one of said receptacles is filled with fluid collected from the patient, additional collected fluid will overflow therefrom to fill the next receptacle and so on until all receptacles are full.

* * * * *